United States Patent
Herron et al.

(10) Patent No.: US 6,365,544 B2
(45) Date of Patent: *Apr. 2, 2002

(54) FISCHER-TROPSCH PROCESSES AND CATALYSTS USING FLUORIDED ALUMINA SUPPORTS

(75) Inventors: Norman Herron, Newark; Leo E. Manzer, Wilmington, both of DE (US); Munirpallam A. Subramanian, Kennett Sq., PA (US)

(73) Assignee: Conoco Inc., Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/314,920

(22) Filed: May 19, 1999

Related U.S. Application Data

(60) Provisional application No. 60/086,372, filed on May 22, 1998, provisional application No. 60/086,405, filed on May 22, 1998, and provisional application No. 60/697,180, filed on Aug. 20, 1998.

(51) Int. Cl.[7] .................... B01J 23/40; B01J 23/42; B01J 27/128; B01J 27/13; C07C 27/00
(52) U.S. Cl. .................. 502/326; 502/327; 502/229; 502/230; 518/700; 518/715
(58) Field of Search ................ 502/326, 327, 502/229, 230; 518/700, 715

(56) References Cited

U.S. PATENT DOCUMENTS

| | | | |
|---|---|---|---|
| 3,268,439 A | 8/1966 | Tupman et al. | 208/112 |
| 3,619,412 A | 11/1971 | Clement et al. | 208/111 |
| 3,711,399 A | 1/1973 | Estes et al. | 208/112 |
| 4,088,671 A | 5/1978 | Kobylinski | 260/449.6 |
| 4,275,046 A | 6/1981 | McVicker et al. | 423/258 |
| 4,413,064 A | 11/1983 | Beuther et al. | 518/715 |
| 4,477,595 A | 10/1984 | Madon | 518/715 |
| 4,513,104 A | 4/1985 | Wright et al. | 518/714 |
| 4,542,122 A | 9/1985 | Payne et al. | 502/325 |
| 4,555,526 A * | 11/1985 | Wakui et al. | 518/717 |
| 4,619,910 A | 10/1986 | Dyer et al. | 502/336 |
| 4,659,681 A | 4/1987 | Rice et al. | 502/5 |
| 4,670,472 A | 6/1987 | Dyer et al. | 518/700 |
| 4,681,867 A | 7/1987 | Dyer et al. | 502/242 |
| 4,766,260 A | 8/1988 | Manzer et al. | 570/168 |
| 4,832,819 A | 5/1989 | Hamner | 208/27 |
| 4,902,838 A | 2/1990 | Manzer et al. | 570/151 |
| 4,919,786 A | 4/1990 | Hamner et al. | 208/27 |
| 4,923,841 A | 5/1990 | Hamner et al. | 502/230 |
| 4,943,672 A | 7/1990 | Hamner et al. | 585/737 |
| 5,243,106 A | 9/1993 | Manzer et al. | 570/166 |
| 5,248,701 A | 9/1993 | Soled et al. | 518/700 |
| 5,348,982 A | 9/1994 | Herbolzheimer et al. | 518/700 |
| 5,393,509 A | 2/1995 | Corbin et al. | 423/465 |
| 5,417,954 A | 5/1995 | Harlow et al. | 423/465 |
| 5,460,795 A | 10/1995 | Corbin et al. | 423/465 |
| 5,559,069 A | 9/1996 | Rao et al. | 502/226 |
| 5,780,381 A * | 7/1998 | Wilson et al. | 502/308 |
| 5,900,159 A * | 5/1999 | Engel et al. | 210/788 |
| 5,919,994 A * | 7/1999 | Rao | 570/176 |
| 5,945,459 A * | 8/1999 | Mauldin | 518/715 |
| 5,968,991 A * | 10/1999 | Mauldin | 518/700 |
| 5,981,608 A * | 11/1999 | Geerlings et al. | 518/715 |
| 6,025,532 A * | 2/2000 | Sage et al. | 570/171 |

FOREIGN PATENT DOCUMENTS

| | | |
|---|---|---|
| DE | 731295 | 8/1936 |
| EP | 142887 | 6/1986 |
| EP | 497436 | 8/1992 |
| WO | WO9719751 | 11/1996 |
| WO | WO9847620 | 10/1998 |

OTHER PUBLICATIONS

PCT Notification of Transmittal of the International Search Report or the Declaration dated Apr. 11, 2000.
PCT International Search Report dated Oct. 15, 1999.
E. Iglesia et al. 1993; In: "Computer–Aided Design of Catalysts," ed. E. R. Becker et al., p.215, New York, Marcel Dekker, Inc.). Month Not Avail.
N. Herron et al. 1993, "Organic Cation Salts of the Tetrafluoroaluminate Anion . . . " J. Am. Chem. Soc. 115:3028–3029, Jan. 1993.

* cited by examiner

*Primary Examiner*—Mark L. Bell
*Assistant Examiner*—Patricia L. Hailey
(74) *Attorney, Agent, or Firm*—Conley, Rose & Tayon, PC

(57) ABSTRACT

A process is disclosed for producing hydrocarbons. The process involves contacting a feed stream comprising hydrogen and carbon monoxide with a catalyst in a reaction zone maintained at conversion-promoting conditions effective to produce an effluent stream comprising hydrocarbons. In accordance with this invention the catalyst used in the process includes at least one catalytic metal for Fischer-Tropsch reactions (e.g., iron, cobalt, nickel and/or ruthenium); and a support selected from the group consisting of an aluminum fluoride and fluorided aluminas.

20 Claims, No Drawings

FISCHER-TROPSCH PROCESSES AND CATALYSTS USING FLUORIDED ALUMINA SUPPORTS

CROSS-REFERENCE TO RELATED APPLICATIONS

This application claims the benefit of U.S. provisional patent application Ser. No. 60/086,372, filed May 22, 1998, U.S. provisional patent application Ser. No. 60/086,405, filed May 22, 1998, and of U.S. provisional patent application Ser. No. 60/097,180, filed Aug. 20, 1998, all of which are incorporated herein by reference in their entirety.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas (i.e., a mixture of carbon monoxide and hydrogen), typically labeled the Fischer-Tropsch process. Particularly, this invention relates to the use of fluorided alumina supported catalysts for the Fischer-Tropsch process.

BACKGROUND OF THE INVENTION

Large quantities of methane, the main component of natural gas, are available in many areas of the world. Methane can be used as a starting material for the production of other hydrocarbons. The conversion of methane to hydrocarbons is typically carried out in two steps. In the first step methane is reformed with water or partially oxidized with oxygen to produce carbon monoxide and hydrogen (i.e., synthesis gas or syngas). In a second step, the syngas is converted to hydrocarbons.

This second step, the preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active metal of Groups 8, 9, 10 (in the New notation for the periodic table of the elements, followed throughout). In particular, iron, cobalt, nickel, and ruthenium have been abundantly used as the catalytically active metals. Cobalt and ruthenium have been found to be most suitable for catalyzing a process in which synthesis gas is converted to primarily hydrocarbons having five or more carbon atoms (i.e., where the $C_5^+$ selectivity of the catalyst is high).

The Fischer-Tropsch reaction involves the catalytic hydrogenation of carbon monoxide to produce a variety of products ranging from methane to higher alkanes and aliphatic alcohols. The methanation reaction was first described in the early 1900's, and the later work by Fischer and Tropsch dealing with higher hydrocarbon synthesis was described in the 1920's.

The Fischer-Tropsch synthesis reactions are highly exothermic and reaction vessels must be designed for adequate heat exchange capacity. Because the feed streams to Fischer-Tropsch reaction vessels are gases while the product streams include liquids and waxes, the reaction vessels must have the ability to continuously produce and remove the desired range of liquid and wax hydrocarbon products. The process has been considered for the conversion of carbonaceous feedstock, e.g., coal or natural gas, to higher value liquid fuel or petrochemicals. The first major commercial use of the Fischer-Tropsch process was in Germany during the 1930's. More than 10,000 B/D (barrels per day) of products were manufactured with a cobalt based catalyst in a fixed-bed reactor. This work has been described by Fischer and Pichler in Ger. Pat. No. 731,295 issued Aug. 2, 1936.

Motivated by production of high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Tex., using powdered iron as the catalyst. Due to disappointing levels of conversion, scale-up problems, and rising natural gas prices, operations at this plant were suspended in 1957. Research has continued, however, on developing Fischer-Tropsch reactors such as slurry-bubble columns, as disclosed in U.S. Pat. No. 5,348,982 issued Sep. 20, 1994.

Commercial practice of the Fischer-Tropsch process has continued from 1954 to the present day in South Africa in the SASOL plants. These plants use iron-based catalysts, and produce gasoline in relatively high-temperature fluid-bed reactors and wax in relatively low-temperature fixed-bed reactors.

Research is likewise continuing on the development of more efficient Fischer-Tropsch catalyst systems and reaction systems that increase the selectivity for high-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution or product selectivity depends heavily on the type and structure of the catalysts and on the reactor type and operating conditions. Accordingly, it is highly desirable to maximize the selectivity of the Fischer-Tropsch synthesis to the production of high-value liquid hydrocarbons, such as hydrocarbons with five or more carbon atoms per hydrocarbon chain.

U.S. Pat. No. 4,659,681 issued on Apr. 21, 1987, describes the laser synthesis of iron based catalyst particles in the 1–100 micron particle size range for use in a slurry reactor for Fischer-Tropsch synthesis.

U.S. Pat. No. 4,619,910 issued on Oct. 28, 1986, and U.S. Pat. No. 4,670,472 issued on Jun. 2, 1987, and U.S. Pat. No. 4,681,867 issued on Jul. 21, 1987, describe a series of catalysts for use in a slurry Fischer-Tropsch process in which synthesis gas is selectively converted to higher hydrocarbons of relatively narrow carbon number range. Reactions of the catalyst with air and water and calcination are specifically avoided in the catalyst preparation procedure. The catalysts are activated in a fixed-bed reactor by reaction with $CO+H_2$ prior to slurrying in the oil phase in the absence of air.

Catalyst supports for catalysts used in Fischer-Tropsch synthesis of hydrocarbons have typically been oxides (e.g., silica, alumina, titania, zirconia or mixtures thereof, such as silica-alumina). It has been claimed that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). The hydrocarbon products prepared by using these catalysts usually have a very wide range of molecular weights.

U.S. Pat. No. 4,477,595 discloses ruthenium on titania as a hydrocarbon synthesis catalyst for the production of $C_5$ to $C_{40}$ hydrocarbons, with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst. U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group 3 or Group 4 metal oxide, e.g., thoria European Patent No. 142,887 discloses a silica supported cobalt catalyst together with zirconium, titanium, ruthenium and/or chromium.

Despite the vast amount of research effort in this field, Fischer-Tropsch catalysts using metal fluoride supports are not known in the art. There is still a great need to identify new catalysts for Fischer-Tropsch synthesis; particularly catalysts that provide high $C_5^+$ hydrocarbon selectivities to maximize the value of the hydrocarbons produced and thus the process economics.

SUMMARY OF THE INVENTION

This invention provides a process and catalyst for producing hydrocarbons, and a method for preparing the catalyst. The process comprises contacting a feed stream comprising hydrogen and carbon monoxide with a catalyst in a reaction zone maintained at conversion-promoting conditions effective to produce an effluent stream comprising hydrocarbons. In accordance with this invention the catalyst used in the process comprises at least one catalytic metal for Fischer-Tropsch reactions (e.g., at least one metal selected from the group consisting of iron, cobalt, nickel and ruthenium); and a support material selected from the group including an aluminum fluoride and fluorided aluminas.

The invention includes a method for the preparation of a supported Fischer-Tropsch catalyst comprising impregnating a support selected from the group including an aluminum fluoride and fluorided aluminas with a catalytic metal for Fischer-Tropsch reactions.

The invention also includes a supported Fischer-Tropsch catalyst comprising at least one catalytic metal for Fischer-Tropsch reactions and a support selected from the group including an aluminum fluoride and fluorided aluminas.

The invention also includes a process for producing hydrocarbons, comprising contacting a feed stream comprising hydrogen and carbon monoxide with a catalyst in a reaction zone maintained at conversion-promoting conditions effective to produce an effluent stream comprising hydrocarbons, said catalyst comprising at least one catalytic metal for Fischer-Tropsch reactions and a support selected from the group including an aluminum fluoride and fluorided aluminas.

DETAILED DESCRIPTION OF THE INVENTION

The feed gases charged to the process of the invention comprise hydrogen, or a hydrogen source, and carbon monoxide. $H_2/CO$ mixtures suitable as a feedstock for conversion to hydrocarbons according to the process of this invention can be obtained from light hydrocarbons such as methane by means of steam reforming, partial oxidation, or other processes known in the art. Preferably the hydrogen is provided by free hydrogen, although some Fischer-Tropsch catalysts have sufficient water gas shift activity to convert some water to hydrogen for use in the Fischer-Tropsch process. It is preferred that the molar ratio of hydrogen to carbon monoxide in the feed be greater than 0.5:1 (e.g., from about 0.67 to 2.5). Preferably, when cobalt, nickel, and/or ruthenium catalysts are used the feed gas stream contains hydrogen and carbon monoxide in a molar ratio of about 2:1; and preferably when iron catalysts are used the feed gas stream contains hydrogen and carbon monoxide in a molar ratio of about 0.67:1. The feed gas may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column, reactive distillation column, or ebullating bed reactors, among others, may be used. Accordingly, the size and physical form of the catalyst particles may vary depending on the reactor in which they are to be used.

A component of the catalysts used in this invention is the support material, which carries the active catalyst component. The support material can comprise an aluminum fluoride or fluorided alumina. Aluminum fluoride is defined as at least one of aluminum fluoride (e.g., alpha-$AlF_3$, beta-$AlF_3$, delta-$AlF_3$, eta-$AlF_3$, gamma-$AlF_3$, kappa-$AlF_3$ and/or theta-$AlF_3$). Preferred are aluminum fluorides which are primarily alpha-$AlF_3$ and/or beta-$AlF_3$.

Fluorided alumina is defined as a composition comprising aluminum, oxygen, and fluorine. The fluoride content of the fluorided alumina can vary over a wide range, from about 0.001% to about 67.8% by weight. Preferred are fluorided aluminas containing from 0.001% to about 10% by weight fluorine. The remainder of the fluorided alumina component will include aluminum and oxygen. The composition may also contain a minor amount (compared to aluminum) of silicon, titanium, phosphorus, zirconium and/or magnesium.

The support material comprising fluorided aluminas and/or an aluminum fluoride may be prepared by a variety of methods. For example, U.S. Pat. Nos. 4,275,046 and 4,902,838 and 5,243,106 disclose the preparation of fluorided alumina by the reaction of alumina with a vaporizable fluorine-containing fluorinating compound. Suitable fluorinating compounds include HF, $CCl_3F$, $CCl_2F_2$, $CHClF_2$, $CH_3CHF_2$, $CCl_2FCClF_2$ and $CHF_3$. U.S. Pat. No. 5,243,106 discloses the preparation of a high purity $AlF_3$ from aluminum sec-butoxide and HF.

Metals can be supported on aluminum fluoride or on fluorided alumina in a variety of ways. For example, U.S. Pat. No. 4,766,260 discloses the preparation of metals such as cobalt on a fluorided alumina support using impregnation techniques to support the metal. U.S. Pat. No. 5,559,069 discloses the preparation of a multiphase catalyst composition comprising various metal fluorides including cobalt fluoride homogeneously dispersed with aluminum fluoride. PCT Int. Publ. No. 97/19751 discloses the preparation of multiphase catalyst compositions comprising metallic ruthenium homogeneously dispersed with various metal fluorides including aluminum fluoride.

Phases of aluminum fluoride such as eta, beta, theta and kappa can be prepared as described in U.S. Pat. No. 5,393,509, U.S. Pat. No. 5,417,954 and U.S. Pat. No. 5,460,795.

Aluminas that have been treated with fluosilicic acid ($H_2SiF_6$) such as those described in European Patent Application No. EP 497,436 can also be used as a support. The disclosed support comprises from about 0.5 to about 10 weight percent of fluorine, from 0.5 to about 5 weight percent of silica and from about 85 to about 99 weight percent of alumina.

Another component of the catalyst of the present invention is the catalytic metal. Preferably the catalytic metal is selected from iron, cobalt, nickel and/or ruthenium. Normally, the metal component is reduced to provide elemental metal (e.g., elemental iron, cobalt, nickel and/or ruthenium) before use. The catalyst must contain a catalytically effective amount of the metal component(s). The amount of catalytic metal present in the catalyst may vary widely. Typically, the catalyst comprises about 1 to 50% by weight (as the metal) of total supported iron, cobalt, nickel and/or ruthenium per total weight of catalytic metal and support, preferably from about 1 to 30% by weight, and still more preferably from about 1 to 10% by weight. Each of the metals can be used individually or in combination, especially cobalt and ruthenium. One preferred catalyst comprises about 10 to 25% by weight (e.g., about 20% by weight) of a combination of cobalt and ruthenium where the ruthenium content is from about 0.001 to about 1 weight %.

The catalyst may also comprise one or more additional promoters or modifiers known to those skilled in the art. When the catalytic metal is iron, cobalt, nickel, and/or ruthenium, suitable promoters include at least one promoter selected from the group consisting of Group 1 metals (i.e., Na, K, Rb, Cs), Group 2 metals (i.e., Mg, Ca, Sr, Ba), Group 11 metals (i.e., Cu, Ag, and Au) Group 3 metals (i.e., Sc, Y and La), Group 4 metals (i.e., Ti, Zr and Hf), Group 5 metals (i.e., V, Nb and Ta), and Rh, Pd, Os, Ir, Pt and Re. Preferably, any additional promoters for the cobalt and/or ruthenium are selected from Sc, Y and La, Ti, Zr, Hf, Rh, Pd, Os, Ir, Pt, Re, Nb, Cu, Ag and Ta. Preferably, any additional promoters for the iron catalysts are selected from Na, K, Rb, Cs, Mg, Ca, Sr and Ba. The amount of additional promoter, if present, is typically between 0.001 and 40 parts by weight per 100 parts of carrier. Catalysts comprising from about to 25% by weight of a combination of cobalt and rhenium, where the rhenium content is from about 0.001 to about 1 weight %; and catalysts comprising from about 10 to 25% by weight of cobalt and both rhenium and ruthenium where the rhenium and ruthenium together total from about 0.001 to about 1 weight % are preferred.

The catalysts of the present invention may be prepared by any of the methods known to those skilled in the art. By way of illustration and not limitation, such methods include impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention may be used in the form of powders, particles, pellets, monoliths, honeycombs, packed beds, foams, and aerogels.

The most preferred method of preparation may vary among those skilled in the art, depending for example on the desired catalyst particle size. Those skilled in the art are able to select the most suitable method for a given set of requirements.

One method of preparing a supported metal catalyst (e.g., a supported cobalt catalyst) is by incipient wetness impregnation of the support with an aqueous solution of a soluble metal salt such as nitrate, acetate, acetylacetonate or the like. Another method involves preparing the supported metal catalyst from a molten metal salt. One preferred method is to impregnate the support with a molten metal nitrate (e.g., $Co(NO_3)_2 \cdot 6H_2O$). Alternatively, the support can be impregnated with a solution of zero valent metal precursor. One preferred method is to impregnate the support with a solution of zero valent cobalt such as $Co_2(CO)_8$, $Co_4(CO)_{12}$ or the like in a suitable organic solvent (e.g., toluene). The impregnated support is dried and reduced with a hydrogen containing gas. The hydrogen reduction step may not be necessary if the catalyst is prepared with zero valent cobalt. In another preferred method, the impregnated support is dried, oxidized with air or oxygen and reduced with a hydrogen containing gas.

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with a hydrogen containing gas at a temperature in the range of from about 75° C. to about 500° C., for about 0.5 to about 24 hours at a pressure of about 1 to about 75 atm. Pure hydrogen may be used in the reduction treatment, as may a mixture of hydrogen and an inert gas such as nitrogen, or a mixture of hydrogen and other gases as are known in the art, such as carbon monoxide and carbon dioxide. Reduction with pure hydrogen and reduction with a mixture of hydrogen and carbon monoxide are preferred. The amount of hydrogen may range from about 1% to about 100% by volume.

The Fischer-Tropsch process is typically run in a continuous mode. In this mode, the gas hourly space velocity through the reaction zone typically may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), and still more preferably, from about 140 psig (1066 kPa) to about 400 psig (2858 kPa).

The products resulting form the process will have a great range of molecular weights. Typically, the carbon number range of the product hydrocarbons will start at methane and continue to the limits observable by modern analysis, about 50 to 100 carbons per molecule. The process is particularly useful for making hydrocarbons having five or more carbon atoms especially when the above-referenced preferred space velocity, temperature and pressure ranges are employed.

The wide range of hydrocarbons produced in the reaction zone will typically afford liquid phase products at the reaction zone operating conditions. Therefore the effluent stream of the reaction zone will often be a mixed phase stream including liquid and vapor phase products. The effluent stream of the reaction zone may be cooled to effect the condensation of additional amounts of hydrocarbons and passed into a vapor-liquid separation zone separating the liquid and vapor phase products. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column where they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following embodiments are to be construed as illustrative, and not as constraining the scope of the present invention in any way whatsoever.

EXAMPLES

General Procedure For Batch Tests

Each of the catalyst samples was treated with hydrogen prior to use in the Fischer-Tropsch reaction. The catalyst sample was placed in a small quartz crucible in a chamber and purged with 500 sccm ($8.3 \times 10^{-6}$ m$^3$/s) nitrogen at room temperature for 15 minutes. The sample was then heated under 100 sccm ($1.7 \times 10^{-6}$ m$^3$/s) hydrogen at 1° C./minute to 100° C. and held at 100° C. for one hour. The catalysts were then heated at 1° C./minute to 400° C. and held at 400° C. for four hours under 100 sccm ($1.7 \times 10^{-6}$ m$^3$/s) hydrogen. The samples were cooled in hydrogen and purged with nitrogen before use.

A 2 mL pressure vessel was heated at either 200° C. or 225° C. under 1000 psig (6994 kPa) of $H_2$:CO (2:1) and maintained at that temperature and pressure for 1 hour. In a typical run, roughly 50 mg of the reduced catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of $C_{11}$–$C_{40}$ were analyzed relative to the internal standard. The lower hydrocarbons were not analyzed since they are masked by the solvent and are also vented as the pressure is reduced.

A $C_{11}^+$ Productivity (g $C_{11}^+$/hour/kg catalyst) was calculated based on the integrated production of the $C_{11}$–$C_{40}$ hydrocarbons per kg of catalyst per hour. The logarithm of the weight fraction for each carbon number 1 n($W_n$/n) was plotted as the ordinate vs. number of carbon atoms in ($W_n$/n) as the abscissa. From the slope, a value of alpha was obtained. Some runs displayed a double alpha as shown in the tables. The results of runs over a variety of catalysts at 200° C. are shown in Table 1 and at 225° C. in Table 2.

Catalyst Preparation

Example 1

Pyridinium AlF$_4$ (25 g), prepared according to the procedure described in N. Herron et al., *J. Am. Chem. Soc.*, 1993, 115, 3028, was spread thinly in a quartz boat in a horizontal tube furnace equipped with a flow of dry air and located in an efficient fume hood. The sample was heated to 800° C. over a period of 1 hour and held there for 30 minutes. The resultant alpha phase AlF$_3$ was collected and stored.

Part of this material (4 g) was slurried into a solution of ruthenium trichloride hydrate (1.5 g) dissolved in methanol (25 mL). The slurry was stirred for 10 minutes and then evaporated to dryness without heating. The recovered dry solid was then calcined in flowing air in a tube furnace at 150° C. for 2 hours after which the gas flow was switched to dry nitrogen. The temperature was quickly ramped to 400° C. and held there as the gas phase was again switched, this time to dry hydrogen. The sample was treated in a hydrogen flow at 400° C. for 1 hour. A catalyst with nominal composition of 10% Ru on alpha-AlF$_3$ was isolated. The material was cooled, flushed with nitrogen and then sealed for transport into an inert atmosphere glove box.

Example 2

Pyridinium AlF$_4$ (25 g), prepared as described in Example 1, was slurried into 50 mL formamide under an inert atmosphere and then the slurry was heated until all solids dissolved. The clear solution was then rapidly heated to boiling in an open container under nitrogen and held there for 30 minutes as pyridine and CO boiled from the solution with effervescence. The solution was slowly cooled yielding a translucent white solid precipitate. The precipitate was filtered and suction dried as a crystalline white material. The recovered white solid was spread thinly in a quartz boat in a horizontal tube furnace equipped with a rapid flow of dry nitrogen and located in an efficient fume hood. The sample was heated to 450° C. over a period of 45 minutes and held there for 4 hours. The resultant beta phase AlF$_3$ was collected and stored.

Ruthenium was deposited onto this support (4 g) exactly as described for the alpha-phase material above (Example 1). A catalyst with nominal composition of 10% Ru on beta-AlF$_3$ was isolated.

Example 3

Pyridinium AlF$_4$ (25 g), prepared as described in Example 1, was slurried into formamide (50 mL) under an inert atmosphere and then the slurry was heated until all solids dissolved. The clear solution was then rapidly heated to boiling in an open container under nitrogen and held there for 5 minutes as pyridine and CO boiled from the solution with effervescence. The solution was removed from the heat source and quickly cooled yielding a translucent white solid precipitate, which was then filtered and suction dried to yield a crystalline white material. The recovered white solid was spread thinly in a quartz boat in a horizontal tube furnace equipped with a rapid flow of dry nitrogen and located in an efficient fume hood. The sample was heated to 450° C. over a period of 45 minutes and held there for 4 hours. The resultant kappa phase AlF$_3$ was collected and stored.

Ruthenium was deposited onto this support (4 g) exactly as described for the alpha-phase material above (Example 1). A catalyst with nominal composition of 10% Ru on kappa-AlF$_3$ was isolated.

Example 4

Pyridinium AlF$_4$ (25 g), prepared as described in Example 1, was slurried into 2,4,6-collidine (50 mL) under an inert atmosphere followed by heating until all solids dissolved. Upon cooling, white needle crystals were collected by filtration and this collidinium salt was suction dried under nitrogen. The recovered solid was dissolved in warm methanol and tetramethylammonium chloride (0.8 g) per gram of the salt was added to the clear solution. After brief stirring, the clear solution was evaporated to dryness. The recovered white solid was spread thinly in a quartz boat in a horizontal tube furnace equipped with a rapid flow of dry air and located in an efficient fume hood. The sample was heated to 450° C. over a period of about 1 hour and held there for 30 minutes. The resultant theta phase AlF$_3$ was collected and stored.

Ruthenium was deposited onto this support (4 g) exactly as described for the alpha-phase material above (Example 1). A catalyst with nominal composition of 10% Ru on theta-AlF$_3$ was isolated.

Example 5

Pyridinium AlF$_4$ (25 g), prepared as described in Example 1, was spread thinly in a quartz boat in a horizontal tube furnace equipped with a flow of dry air and located in an efficient fume hood. The sample was heated to 375° C. over a period of about 45 minutes and held there for 30 minutes. The resultant eta phase AlF$_3$ was collected and stored.

Ruthenium was deposited onto this support (4 g) exactly as described for the alpha-phase material above (Example 1). A catalyst with nominal composition of 10% Ru on eta-AlF$_3$ was isolated.

Example 6

An aqueous solution of $(NH_3)_6RuCl_6$ (3.0637 g) was slurried with a crushed commercial sample of fluorided alumina (9.0000 g) obtained from Engelhard (A-4352) and calcined at 600° C. in air prior to use. The water was slowly evaporated and the residue dried at 110° C. The dried solids were treated in hydrogen for 4 hours at 400° C. A catalyst (9.718 g) with a nominal composition of 10% Ru on fluorided alumina was isolated.

Example 7

$Co(NO_3)_2.6H_2O$ (14.8305 g) and AlF$_3$ (7.000 g) were mixed together in a beaker on a hot plate and heated to 75° C. The solid chunks were then treated with hydrogen at 400° C. for 4 hours, then ground and treated again with hydrogen at 400° C. for 4 hours. A catalyst (9.583 g) with a nominal composition of 30% Co/AlF$_3$ was isolated.

Example 8

The catalyst was prepared in the same manner as that of Example 6.

Example 9

The catalyst was prepared in the same manner as that of Example 2.

Example 10

The catalyst was prepared in the same manner as that of Example 7.

Example 11

Gamma-alumina (10 g) was crushed to 60–80 mesh (0.25–0.18 mm) size and then placed in a quartz boat in a horizontal tube furnace equipped with a flow of 90 mL/min dry nitrogen and 10 mL/min fluoroform (CHF$_3$) and located in an efficient fume hood. The sample was heated to 350° C. over a period of 30 minutes and held there for 30 minutes. The resultant fluorided alumina was collected and stored.

A sample of this material (10 g) was slurried into a solution of 3.75 g ruthenium trichloride hydrate dissolved in methanol (25 mL). The slurry was stirred for about 10 minutes and then evaporated to dryness without heating. The recovered dry solid was then calcined in flowing dry air in a tube furnace at 150° C. for two hours and then the gas flow was switched to dry nitrogen. The temperature was quickly ramped to 450° C. and held there as the gas phase was again switched, this time to dry hydrogen. The sample was reduced in hydrogen flow at 450° C. for 1 hour. The material was cooled and flushed with nitrogen and then sealed for transport into an inert atmosphere glove box. The recovered catalyst was bottled and sealed for storage inside the glove box until Fischer-Tropsch testing could be completed. The catalyst had a nominal composition of 10% Ru/fluorided alumina.

Example 12

An aqueous solution of $Co(NO_3)_2.6H_2O$ (15.63 g) was slurried with a crushed commercial sample of fluorided alumina (7.000 g) obtained from Engelhard (Al-4352) and calcined in air at 500° C. prior to use. The water was slowly evaporated and the residue dried at 110° C. The dried solids were treated in hydrogen for 4 hours at 400° C. A catalyst (10.661 g) with a nominal composition of 30% Co on fluorided alumina was isolated.

Example 13

An aqueous solution of $(NH_3)_6RuCl_6$ (1.5318 g) was slurried with a fluorided alumina (4.5000 g) obtained by treating gamma-alumina with HF at 400° C. The water was slowly evaporated and the residue dried at 110° C. The dried solids were treated in hydrogen for 4 hours at 400° C. A catalyst with a nominal composition of 10% Ru on fluorided alumina was isolated.

Example 14

An aqueous solution of $(NH_3)_6RuCl_6$ (3.0637 g) was slurried with a commercial sample of fluorided alumina (9.0000 g) obtained from Engelhard (Al-4198) and calcined in air at 600° C. prior to use. The water was slowly evaporated and the residue dried at 110° C. The dried solids were treated in hydrogen for 4 hours at 400° C. A catalyst (9.669 g) with a nominal composition of 10% Ru on fluorided alumina was isolated.

Example 15

Engelhard fluorided alumina (Al-4352, 10 g) was calcined in dry air at 600° C. for four hours. Some of this material (1 g) was crushed to 60–80 mesh (0.25–0.18 mm) size and slurried into a solution of cobalt chloride hydrate (0.50 g) and magnesium nitrate (0.05 g) as a promoter in methanol (25 mL). The slurry was stirred for about 10 minutes and then evaporated to dryness without heating. The recovered dry solid was then calcined in flowing dry air in a tube furnace at 150° C. for two hours and then the gas flow was switched to dry nitrogen. The temperature was quickly ramped to 450° C. and held there as the gas phase was again switched, this time to dry hydrogen. The sample was reduced in hydrogen flow at 450° C. for 1 hour. The material was cooled and flushed with nitrogen overnight and then sealed for transport into an inert atmosphere glove box. The recovered catalyst was bottled and sealed for storage inside the glove box until Fischer-Tropsch (FT) testing could be completed. The catalyst had a nominal composition of 20% Co/fluorided alumina.

Example 16

Calcined Engelhard fluorided alumina (Al-4352, 1 g) was crushed to 60–80 mesh (0.25–0.18 mm) size and then loaded into an inert atmosphere glove box. The material was slurried into a solution of tetracobaltdodecacarbonyl (0.50 g) in a minimum volume of dry toluene. The slurry was stirred for about 10 minutes and then evaporated to dryness using a vacuum pump. The recovered dry solid was then placed in a quartz boat in a horizontal tube furnace equipped with a flow of dry hydrogen. The sample was heated to 200° C. in dry hydrogen at 10° C./minute and then held for 30 minutes. The material was cooled, flushed with dry nitrogen, and sealed for transport into an inert atmosphere glove box, The recovered catalyst was bottled and sealed for storage inside the glove box until Fischer-Tropsch testing could be completed. The catalyst had a nominal composition of 20% Co/fluorided alumina.

Example 17

Alpha phase $AlF_3$ (1 g) prepared as described in Example 1 was loaded into an inert atmosphere glove box and then slurried into a solution of tetracobaltdodecacarbonyl (0.50 g) in a minimum amount of toluene. The slurry was stirred for about 10 minutes and then evaporated to dryness using a vacuum pump. The recovered dry solid was then placed in a quartz boat in a horizontal tube furnace equipped with a flow of dry hydrogen. The sample was heated to 200° C. in dry hydrogen at 10° C./min and then held for 30 mins. The material was cooled, flushed with dry nitrogen, and sealed for transport into an inert atmosphere glove box. The recovered catalyst was bottled and sealed for storage inside the glove box until FT testing could be completed. The catalyst had a nominal composition of 20% Co/alpha-$AlF_3$.

Example 18

Engelhard (Al-4352) fluorided alumina (1 g) was slurried into a solution of ruthenium trichloride hydrate (0.375 g) and nickel chloride hydrate (0.125 g) in methanol (10 mL). From this point forward the procedure followed was identical to that described in Example 19. A catalyst with a nominal composition of 10% Ru and 5% Ni on fluorided alumina was isolated.

Example 19

Engelhard fluorided alumina (Al-4352, 10 g) was calcined in dry air at 600° C. for four hours. Some of this material (1 g) was crushed to 60–80 mesh (0.25–0.18 mm) size. This was slurried into a solution containing cobalt chloride hydrate (0.50 g) and anhydrous nickel chloride (0.125 g) in methanol (10 mL). The slurry was stirred for about 10 minutes and then evaporated to dryness without heating. The recovered dry solid was then calcined in flowing dry air in a tube furnace at 150° C. for two hours, then the gas flow was switched to dry nitrogen. The temperature was quickly ramped to 450° C. and held there as the gas phase was again switched, this time to dry hydrogen. The sample was reduced in hydrogen flow at 450° C. for 1 hour. The material was cooled and flushed with nitrogen and then sealed for transport into an inert atmosphere glove box. The recovered catalyst was bottled and sealed for storage inside the glove box until Fischer-Tropsch testing could be completed. The catalyst had a nominal composition of 20% Co/5% Ni/fluorided alumina.

Example 20

Engelhard fluorided alumina (Al-4352, 10 g) was calcined in dry air at 600° C. for four hours. Some of this material (1 g) was crushed to 60–80 mesh (0.25–0.18 mm) size. This was slurried into a solution containing ruthenium chloride hydrate (0.375 g) and palladium tetraamine chloride (0.025 g) in methanol (10 mL). The slurry was stirred for about 10 minutes and then evaporated to dryness without heating. The recovered dry solid was then calcined in flowing dry air in a tube furnace at 150° C. for two hours and then cooled. The sample was left in flowing air overnight, then the gas flow was switched to dry nitrogen. The temperature was quickly ramped to 450° C. and held there as the gas phase was again switched, this time to dry hydrogen. The sample was reduced in hydrogen flow at 450° C. for 1 hour. The material was cooled and flushed with nitrogen and then sealed for transport into an inert atmosphere glove box. The recovered catalyst was bottled and sealed for storage inside the glove box until Fischer-Tropsch testing could be completed. The catalyst had a nominal composition of 10% Ru/1% Pd/fluorided alumina.

Example 21

Engelhard fluorided alumina (Al-4352, 10 g) was calcined in dry air at 600° C. for four hours. Some of this material (1 g) was crushed to 60–80 mesh (0.25–0.18 mm) size. This was slurried into a solution containing cobalt chloride hydrate (0.50 g) and palladium tetraamine chloride (0.025 g) in methanol (10 mL). The drying and calcining procedure was that used in Example 20. The catalyst had a nominal composition of 20% Co/1% Pd/fluorided alumina.

Example 22

Alumina (UCI 105-2, 10 g) was heated in fluoroform ($CHF_3$) for one hour at 500° C. to fluorinate it. This material was collected and stored.

UCI fluorided alumina (5 g) was slurried into a solution of ruthenium chloride hydrate (1.9 g) in methanol (50 mL). The drying and calcining procedure was that used in Example 20. The catalyst had a nominal composition of 10% Ru/fluorided alumina.

Example 23

Engelhard (Al-4352) fluorided alumina (10 g) was slurried into a solution of nickel chloride (5 g) and magnesium nitrate (0.5 g) in methanol (25 mL). The slurry was vigorously stirred for 10 minutes and then evaporated to dryness at low temperature. The recovered solid was heated in flowing air at 150° C. for 2 hours and then switched to flowing nitrogen and the temperature ramped to 400° C. When the temperature had equilibrated at 400° C., the gas flow was changed to hydrogen and the sample reduced at 400° C. for 1 hour. The sample was cooled in hydrogen and then flushed with nitrogen before transport into a nitrogen filled glove box for collection. The sample was quite air sensitive and was handled only under nitrogen and samples for testing were prepared inside the glove box. A catalyst with a nominal composition of 20% Ni and 0.5% Mg on fluorided alumina was isolated.

Example 24

Engelhard fluorided alumina (C500-196, 1 g) was calcined in dry air at 600° C. for four hours. This material was then crushed to 60–80 mesh (0.25–0.18 mm) size. This was slurried into a solution containing cobalt chloride hydrate (0.5 g) in methanol (10 mL). The slurry was stirred for about 10 minutes and then evaporated to dryness without heating. The recovered dry solid was then calcined in flowing dry air in a tube furnace at 150° C. for two hours, then the gas flow was switched to dry nitrogen. The temperature was quickly ramped to 450° C. and held there as the gas phase was again switched, this time to dry hydrogen. The sample was reduced in hydrogen flow at 450° C. for 1 hour. The gas phase was again switched to dry nitrogen while the sample cooled. It was determined that there was incomplete reduction (sample was still blue at one end of the furnace boat). The tube was then sealed for transport into an inert atmosphere glove box. The catalyst was mixed well in a beaker and placed in the furnace boat again. It was placed in a flow of dry nitrogen while the temperature was quickly ramped to 450° C. The gas phase was switched to dry hydrogen and the sample was reduced at 450° C. for an additional 30 minutes. The material was cooled and flushed with nitrogen overnight and then sealed for transport into an inert atmosphere glove box. The recovered catalyst was bottled and sealed for storage inside the glove box until Fischer-Tropsch testing could be completed. The catalyst had a nominal composition of 20% Co/fluorided alumina.

Example 25

Engelhard fluorided alumina (C500-196, 1 g) was calcined in dry air at 600° C. for four hours. This material was then crushed to 60–80 mesh (0.25–0.18 mm) size. This was slurried into a solution containing ruthenium chloride hydrate (0.375 g) in methanol (25 mL). The drying and calcining procedure was that used in Example 20. The catalyst had a nominal composition of 10% Ru/fluorided alumina.

Example 26

A sample of Engelhard fluorided alumina (Al-4352, 10 g) was calcined in flowing dry air at 600° C. for four hours. This material was then crushed to 60–80 mesh (0.25–0.18 mm) size and loaded into an inert atmosphere glove box. Cobalt was then deposited onto this support (10 g) as described in Example 16. The catalyst had a nominal composition of 20% Co/fluorided alumina.

Example 27

Engelhard fluorided alumina (Al-4352, 10 g) was calcined in dry air at 600° C. for four it hours. This material was then crushed to 60–80 mesh (0.25–0.18 mm) size. This was slurried into a solution of ruthenium chloride hydrate (3.75 g) in methanol (25 mL). The slurry was stirred for 10 minutes and then evaporated to dryness without heating. The recovered solid was re-slurried into a solution of anhydrous nickel chloride (1.25 g) in methanol (25 mL) and stirred for 10 minutes and then evaporated to dryness. The recovered dry solid was calcined in flowing dry air in a tube furnace at 150° C. for two hours, then the gas flow was switched to dry nitrogen. The temperature was quickly ramped to 450° C. and held there as the gas phase was again switched, this time to dry hydrogen. The sample was reduced in hydrogen flow at 450° C. for 1 hour. The material was cooled and flushed with nitrogen and then bottled and sealed for storage inside an inert atmosphere glove box until Fischer-Tropsch testing could be completed. The catalyst had a nominal composition of 10% Ru/5% Ni/fluorided alumina.

Example 28

Engelhard fluorided alumina (Al-4352, 10 g) was calcined in dry air at 600° C. for four hours. This material was then crushed to 60–80 mesh (0.25–0.18 mm) size. This was slurried into a solution of into a solution of ruthenium chloride hydrate (3.75 g) and palladium tetraamine chloride (0.25 g) in methanol (25 mL). The drying and calcining procedure was that used in Example 20. The catalyst had a nominal composition of 10% Ru/1% Pd/fluorided alumina.

Example 29

$Co(NO_3)_2 \cdot 6H_2O$ (14.8148 g) was melted at 75° C. on a hot plate. An aqueous solution of $(NH_3)_6RuCl_3$ (0.3064 g) was stirred into the molten cobalt nitrate. This cobalt-ruthenium solution was then slurried with a crushed commercial sample of fluorided alumina (6.9000 g) obtained from Engelhard (Al-4352) which was calcined in air at 600° C. prior to use. The water was slowly evaporated and the residue dried at about 110° C. The dried solids were calcined at 350° C. for 0.5 hours and then treated with hydrogen for 6 hours at 500° C. A catalyst (8.7053 g) with a nominal composition of 30% Co/1% Ru on fluorided alumina was isolated.

Example 30

$Co(NO_3)_2 \cdot 6H_2O$ (14.8148 g) was melted at 75° C. on a hot plate. An aqueous solution of $(NH_3)_6RuCl_3$ (0.1532 g) was stirred into the molten cobalt nitrate. This cobalt-ruthenium solution was then slurried with a crushed commercial sample of fluorided alumina (6.9500 g) obtained from Engelhard (Al-4352) which was calcined in air to 600° C. prior to use. The water was slowly evaporated and the residue dried at about 110° C. The dried solids were calcined at 350° C. for 0.5 hours and then treated with hydrogen for 6 hours at 500° C. A catalyst (8.7053 g) with a nominal composition of 30% Co/0.5% Ru on fluorided alumina was isolated.

Example 31

Engelhard fluorided alumina (C500-196, 1 g) was calcined in dry air at 600° C. for four hours. This material was then crushed to 60–80 mesh (0.25–0.18 mm) size. This was slurried into a solution containing 0.40 g ruthenium chloride hydrate and palladium tetraanine chloride (0.025 g) in methanol (10 mL). The drying and calcining procedure was that used in Example 20. The catalyst had a nominal composition of 10% Ru/1% Pd/fluorided alumina.

Example 32

Engelhard fluorided alumina (C500-196, 10 g) was calcined in dry air at 600° C. for four hours. This material was then crushed to 60–80 mesh (0.25–0.18 mm) size. This was slurried into a solution containing 0.40 g ruthenium chloride hydrate and palladium tetraamine chloride (0.025 g) in methanol (10 mL). The drying and calcining procedure was that used in Example 20. The catalyst had a nominal composition of 1% Ru/0.1% Pd/fluorided alumina.

Example 33

$Co(NO_3)_2 \cdot 6H_2O$ (9.8768 g) was melted at 75° C. on a hot plate. A solution of $Ru(CH_3COCHCOCH_3)_3$ (0.1971 g) in acetonitrile was thoroughly mixed into the molten cobalt nitrate. This cobalt-ruthenium mixture was then slurried with a crushed commercial sample of fluorided alumina (7.9500 g) obtained from Engelhard (C500–196). The water was slowly evaporated and the residue dried at about 110° C. The dried solids were calcined at 560° C. in air for 5 hours and then treated with hydrogen for 16 hours at 500° C. A catalyst (10.0823 g) with a nominal composition of 20% Co/0.5% Ru on fluorided alumina was isolated.

Example 34

$Co(NO_3)_2 \cdot 6H_2O$ (9.8768 g) was melted at 75° C. on a hot plate. A solution of $Ru(CH_3COCHCOCH_3)_3$ (0.0985 g) in acetonitrile was thoroughly mixed into the molten cobalt nitrate. This cobalt-ruthenium mixture was then slurried with a crushed commercial sample of fluorided alumina (7.9750 g) obtained from Engelhard (C500-196). The water was slowly evaporated and the residue dried at about 110° C. The dried solids were calcined at 560° C. in air for 5 hours and then treated with hydrogen for 16 hours at 500° C. A catalyst (10.1672 g) with a nominal composition of 20% Co/0.25% Ru on fluorided alumina was isolated.

Example 35

$Co(NO_3)_2.6H_2O$ (9.8768 g) was melted at 75° C. on a hot plate. This cobalt melt was then slurried with a crushed commercial sample of fluorided alumina (8.0000 g) obtained from Engelhard (C500-196). The water was slowly evaporated and the residue dried at about 110° C. The dried solids were calcined at 560° C. in air for 5 hours and then treated with hydrogen for 16 hours at 500° C. A catalyst (10.055 g) with a nominal composition of 20% Co on fluorided alumina was isolated.

Example 36

Engelhard fluorided alumina (Al-4352, 1 g) was calcined in dry air at 600° C. for four hours. This material was then crushed to 60–80 mesh (0.25–0.18 mm) size. This was slurried into a solution containing ruthenium chloride hydrate 0.40 g) in methanol (10 mL). The slurry was stirred for about 10 minutes and then evaporated to dryness without heating. The recovered dry solid was then calcined in flowing dry air in a tube furnace at 150° C. for one hour. The dry material was then loaded into an inert atmosphere glove box and then slurried into a solution of tetracobaltdodecacarbonyl (0.50 g) in a minimum amount of toluene. The slurry was stirred for about 10 minutes and then evaporated to dryness using a vacuum pump. The recovered dry solid was then placed in a quartz boat in a horizontal tube furnace equipped with a flow of dry hydrogen. The sample was heated to 200° C. in dry hydrogen at 10° C./min and then held for 30 mins. The material was cooled, flushed with dry nitrogen overnight, and bottled and sealed for storage inside the glove box until Fischer-Tropsch testing could be completed. The catalyst had a nominal composition of 1% Ru/20% Co/fluorided alumina.

Example 37

Alpha phase $AlF_3$ (1 g) prepared as described in Example 1 was loaded into an inert atmosphere glove box and then slurried into a solution containing ruthenium chloride hydrate (0.40 g) in methanol (10 mL). The slurry was stirred for about 10 minutes and then evaporated to dryness without heating. The recovered dry solid was then calcined in flowing dry air in a tube furnace at 150° C. for one hour. The dry material was then loaded into an inert atmosphere glove box and slurried into a solution of tetracobaltdodecacarbonyl (0.50 g) in a minimum amount of toluene. The slurry was stirred for about 10 minutes and evaporated to dryness using a vacuum pump. The recovered dry solid was placed in a quartz boat in a horizontal tube furnace equipped with a flow of dry hydrogen. The sample was heated to 200° C. in dry hydrogen at 10° C./minute and held for 30 minutes. The material was cooled, flushed with dry nitrogen, and bottled and sealed for storage inside the glove box until Fischer-Tropsch testing could be completed. The catalyst had a nominal composition of 1% Ru/20% Co/alpha-$AlF_3$.

Example 38

A second sample of 10 g alpha $AlF_3$ was slurried into a solution of tetracobaltdodecacarbonyl (5.00 g) in a minimum amount of toluene and was treated exactly the same as Example 17 above, (except the tube furnace was closed throughout the reduction process). The catalyst had a nominal composition of 20% Co/alpha-$AlF_3$.

Example 39

Engelhard fluorided alumina (C500-196, 1 g) was calcined in dry air at 600° C. for four hours. This material was then crushed to 60–80 mesh (0.25–0.18 mm) size. This was slurried into a solution containing ruthenium chloride hydrate (0.40 g) in methanol (10 mL). The slurry was stirred for about 10 minutes and then evaporated to dryness without heating. The recovered dry solid was calcined in flowing dry air in a tube furnace at 150° C. for one hour. The dry material was loaded into an inert atmosphere glove box and then slurried into a solution of tetracobaltdodecacarbonyl (0.50 g) in a minimum amount of toluene. The drying and calcining procedure was that used in Example 37. The catalyst had a nominal composition of 1% Ru/20% Co/fluorided alumina.

Example 40

Engelhard fluorided alumina (C500-196, 1 g) was calcined in dry air at 600° C. for four hours. This material was then crushed to 60–80 mesh (0.25–0.18 mm) size. This was slurried into a solution of tetracobaltdodecacarbonyl (0.50 g) in a minimum amount of toluene. The drying and calcining procedure was that used in Example 37. The catalyst had a nominal composition of 20% Co/fluorided alumina.

Example 41

$Co(NO_3)_2.6H_2O$ (4.9384 g) was melted at 75° C. on a hot plate. This cobalt melt was then slurried with a crushed commercial sample of fluorided alumina (4.0000 g) obtained from Engelhard (Al-4352) which was calcined at 600° C. before use. The water was evaporated and the residue dried at about 80° C. The dried solids were calcined at 0.5° C. per minute in air until the temperature was 350° C. The calcination was then continued for 0.5 hour and then cooled to room temperature. It was then treated in a tube furnace as follows: (1) heated to 100° C. in Ar to remove $O_2$ and $H_2O$; (2) the reaction gas was switched to $H_2$ and the catalyst was reduced at 450° C. for 8 hours with a heating rate of 0.2/min; (3) after reduction, the sample was cooled to room temperature in hydrogen. A catalyst (10.055) with a nominal composition of 20% Co on fluorided alumina was isolated.

Example 42

$Co(NO_3)_2.6H_2O$ (4.9384 g) was melted at 75° C. on a hot plate. $Ru(NO)(NO_3)_3$ (0.0159 g) was dissolved in a minimum amount of water. This cobalt melt and the ruthenium salt solution were mixed and the mixture was then slurried with a crushed commercial sample of fluorided alumina (3.9950 g) obtained from Engelhard (Al-4352) which was calcined at 550° C. before use. The water was evaporated and the residue dried at about 80° C. The dried solids were calcined at 0.5° C. per minute in air until the temperature was 350° C. The calcination was then continued for 0.5 hour and then cooled to room temperature. It was then treated in a tube furnace as follows: (1) heated to 100IC in Ar to remove $O_2$ and $H_2O$; (2) the reaction gas was switched to $H_2$ and the catalyst was reduced at 450° C. for 12 hours with a heating rate of 0.2/min; (3) after reduction, the sample was cooled to room temperature in hydrogen. A catalyst (4.7598 g) with a nominal composition of 20% Co/0.1% Ru on fluorided alumina was isolated.

Example 43

Co(NO$_3$)$_2$.6H$_2$O (4.9384 g) was melted at 75° C. on a hot plate. Re$_2$O$_7$ (0.0650 g) was dissolved in a minimum amount of water. This cobalt melt and the rhenium oxide solution were mixed and the mixture was then slurried with a crushed commercial sample of fluorided alumina (3.9950 g) obtained from Engelhard (Al-4352) which was calcined at 550° C. before use. The water was evaporated and the residue dried at about 80° C. The dried solids were calcined at 0.5° C. per minute in air until the temperature was 350° C. The calcination was then continued for 0.5 hour and then cooled to room temperature. It was then treated in a tube furnace as follows: (1) heated to 100° C. in Ar to remove O$_2$ and H$_2$O; (2) the reaction gas was switched to H$_2$ and the catalyst was reduced at 450° C. for 12 hours with a heating rate of 0.2/min; (3) after reduction, the sample was cooled to room temperature in hydrogen. A catalyst (4.7598 g) with a nominal composition of 20% Co/1.0% Re on fluorided alumina was isolated.

TABLE 1

(200° C.)

| Ex. No. | Catalyst | C$_{11}$$^+$ Productivity | Alpha |
|---|---|---|---|
| 1 | 10% Ru/alpha-AlF$_3$ | 123 | 0.87 |
| 2 | 10% Ru/beta-AlF$_3$ | 167 | 0.82 |
| 3 | 10% Ru/kappa-AlF$_3$ | 44.2 | 0.85 |
| 4 | 10% Ru/theta-AlF$_3$ | 118 | 0.85 |
| 5 | 10% Ru/eta-AlF$_3$ | 60.3 | 0.84 |
| 6 | 10% Ru/Al$_2$O$_3$(F) | 132 | 0.87 |
| 7 | 30% Co/AlF$_3$ | 67.5 | 0.91 |

TABLE 2

(225° C.)

| Ex. No. | Catalyst | C$_{11}$$^+$ Productivity | Alpha |
|---|---|---|---|
| 8 | 10% Ru/Al$_2$O$_3$(F) | 241 | 0.85 |
| 9 | 10% Ru/beta-AlF$_3$ | 79.6 | 0.82/0.95 |
| 10 | 30% Co/AlF$_3$ | 159 | 0.86/0.95 |
| 11 | 10% Ru/Al$_2$O$_3$(F) | 321 | 0.81/0.93 |
| 12 | 30% Co/Al$_2$O$_3$(F) | 87.9 | 0.81/0.92 |
| 13 | 10% Ru/Al$_2$O$_3$(F) | 171 | 0.88/0.99 |
| 14 | 10% Ru/Al$_2$O$_3$(F) | 316 | 0.86/0.96 |
| 15 | 20% Co/Al$_2$O$_3$(F)(Mg) | 23 | 0.81/0.85 |
| 16 | 20% Co/Al$_2$O$_3$(F) | 134 | 0.86 |
| 17 | 20% Co/alpha-AlF$_3$ | 158 | 0.85/0.93 |
| 18 | 10% Ru/5% Ni/Al$_2$O$_3$(F) | 202 | 0.79/0.9 |
| 19 | 20% Co/5% Ni/Al$_2$O$_3$(F) | 6.9 | 0.75/0.89 |
| 20 | 10% Ru/Al$_2$O$_3$(F)(Pd) | 325 | 0.91 |
| 21 | 20% Co/Al$_2$O$_3$(F)(Pd) | 20.3 | 0.79/0.91 |
| 22 | 10% Ru/Al$_2$O$_3$(F) | 205 | 0.86/0.94 |
| 23 | 20% Ni/Al$_2$O$_3$(F)(Mg) | 27.6 | 0.9 |
| 24 | 20% Co/Al$_2$O$_3$(F) | 29 | 0.8/0.91 |
| 25 | 10% Ru/Al$_2$O$_3$(F) | 613 | 0.92 |
| 26 | 20% Co/Al$_2$O$_3$(F) | 233 | 0.88 |
| 27 | 10% Ru/5% Ni/Al$_2$O$_3$(F) | 36.7 | 0.77/0.89 |
| 28 | 10% Ru/Al$_2$O$_3$(F)(Pd) | 519 | 0.9 |
| 29 | 30% Co/1% Ru/Al$_2$O$_3$(F) | 344 | 0.89 |
| 30 | 30% Co/0.5% Ru/Al$_2$O$_3$(F) | 316 | 0.89 |
| 31 | 10% Ru/Al$_2$O$_3$(F)(Pd) | 466 | 0.92 |
| 32 | 1% Ru/Al$_2$O$_3$(F)(Pd) | 53.7 | 0.86 |
| 33 | 20% Co/0.5% Ru/Al$_2$O$_3$(F) | 175 | 0.87 |
| 34 | 20% Co/0.25% Ru/Al$_2$O$_3$(F) | 173 | 0.87 |
| 35 | 20% Co/Al$_2$O$_3$(F) | 159 | 0.86 |
| 36 | 20% Co/1% Ru/Al$_2$O$_3$(F) | 172 | 0.89 |
| 37 | 20% Co/1% Ru/alpha-AlF$_3$ | 22.8 | 0.76/0.88 |
| 38 | 20% Co/alpha-AlF$_3$ | 295 | 0.93 |
| 39 | 20% Co/1% Ru/Al$_2$O$_3$(F) | 151 | 0.89 |
| 40 | 20% Co/Al$_2$O$_3$(F) | 257 | 0.89 |
| 41 | 20% Co/Al$_2$O$_3$(F) | 284 | 0.91 |

TABLE 2-continued (225° C.)

| Ex. No. | Catalyst | C$_{11}$$^+$ Productivity | Alpha |
|---|---|---|---|
| 42 | 20% Co/0.1% Ru/Al$_2$O$_3$(F) | 367 | 0.89 |
| 43 | 20% Co/1.0% Re/Al$_2$O$_3$(F) | 485 | 0.89 |

General Procedure For Continuous Tests

The catalyst testing unit was composed of a syngas feed system, a tubular reactor, which had a set of wax and cold traps, back pressure regulators, and three gas chromatographs (one on-line and two off-line).

The carbon monoxide was purified before being fed to the reactor over a 22% lead oxide on alumina catalyst placed in a trap to remove any iron carbonyls present. The individual gases or mixture of the gases were mixed in a 300 mL vessel filled with glass beads before entering the supply manifold feeding the reactor.

The reactor was made of ⅜ in. (0.95 cm) O.D. by ¼ in. (0.63 cm) I.D. stainless steel tubing. The length of the reactor tubing was 14 in. (35.6 cm). The actual length of the catalyst bed was 10 in. (25.4 cm) with 2 in. (5.1 cm) of 25/30 mesh (0.71/0.59 mm) glass beads and glass wool at the inlet and outlet of the reactor.

The wax and cold traps were made of 75 mL pressure cylinders. The wax traps were set at 140° C. while the cold traps were set at 0° C. The reactor had two wax traps in parallel followed by two cold traps in parallel. At any given time products from the reactor flowed through one wax and one cold trap in series. Following a material balance period, the hot and cold traps used were switched to the other set in parallel, if needed. The wax traps collected a heavy hydrocarbon product distribution (usually between C$_6$ and above) while the cold traps collected a lighter hydrocarbon product distribution (usually between C$_3$ and C$_{20}$). Water, a major product of the Fischer-Tropsch process was collected in both the traps.

General Analytical Procedure

The uncondensed gaseous products from the reactors were analyzed using a common on-line HP Refinery Gas Analyzer. The Refinery Gas Analyzer was equipped with two thermal conductivity detectors and measured the concentrations of CO, H$_2$, N$_2$, CO$_2$, CH$_4$, C$_2$ to C$_5$ alkenes/alkanes/isomers and water in the uncondensed reactor products.

The products from each of the hot and cold traps were separated into an aqueous and an organic phase. The organic phase from the hot trap was usually solid at room temperature. A portion of this solid product was dissolved in carbon disulfide before analysis. The organic phase from the cold trap was usually liquid at room temperature and was analyzed as obtained. The aqueous phase from the two traps was combined and analyzed for alcohols and other oxygenates.

Two off-line gas chromatographs equipped with flame ionization detectors were used for the analysis of the organic and aqueous phases collected from the wax and cold traps.

Catalyst Testing Procedure

Catalyst (3 g) to be tested was mixed with 4 grams of 25/30 mesh (0.71/0.59 mm) and 4 grams of 2 mm glass beads. The 14 in. (35.6 cm) tubular reactor was first loaded with 25/30 mesh (0.71/0.59 mm) glass beads so as to occupy 2 in. (5.1 cm) length of the reactor. The catalyst/glass bead mixture was then loaded and occupied 10 in. (25.4 cm) of the reactor length. The remaining 2 in. (5.1 cm) of reactor length was once again filled with 25/30 mesh (0.71/0.59 mm) glass beads. Both ends of the reactor were plugged with glass wool.

Catalyst activation was subsequently carried out using the following procedure. The reactor was heated to 120° C. under nitrogen flow (100 cc/min and 40 psig (377 kPa)) at a rate of 1.5° C./min. The reactor was maintained at 120° C. under these conditions for two hours for drying of the catalyst. At the end of the drying period, the flow was switched from nitrogen to hydrogen. The reactor was heated under hydrogen flow (100 cc/min and 40 psig (377 kPa)) at a rate of 1.4° C./min. to 350° C. The reactor was maintained at 350° C. under these conditions for sixteen hours for catalyst reduction. At the end of the reduction period, the flow was switched back to nitrogen and the reactor cooled to reaction temperature (usually 220° C.).

The reactor was pressurized to the desired reaction pressure and cooled to the desired reaction temperature. Syngas, with a 2:1 $H_2$/CO ratio was then fed to the reactor when reaction conditions were reached.

The first material balance period started at about four hours after the start of the reaction. A material balance period lasted for between 16 to 24 hours. During the material balance period, data was collected for feed syngas and exit uncondensed gas flow rates and compositions, weights and compositions of aqueous and organic phases collected in the wax and cold traps, and reaction conditions such as temperature and pressure. The information collected was then analyzed to get a total as well as individual carbon, hydrogen and oxygen material balances. From this information, CO Conversion (%), Selectivity/Alpha plot for all ($C_1$ to $C_{40}$) of the hydrocarbon products, $C_5$+ Productivity (g/hr/kg cat), weight percent $CH_4$ in hydrocarbon products (%) and other desired reactor outputs were calculated.

The results obtained from the continuous-flow Fischer-Tropsch catalyst testing unit is shown in Table 3.

This table lists the catalyst composition, CO Conversion (%), Alpha value from the Anderson-Shultz-Flory plot of the hydrocarbon product distribution, $C_5$+ Productivity (g $C_5$+/hour/kgcatalyst) and weight percent methane in the total hydrocarbon product (%).

The temperature was 220° C., the pressure was between 340 psig (2445 kPa) to 362 psig (2597 kPa) and the space velocity was 2 NL/hour/g. cat. for all the examples in Table 3.

Catalyst Preparation

Example 44

The catalyst was prepared in the same manner as that of Example 2.

Example 45

The catalyst was prepared in the same manner as that of Example 4.

Example 46

$(NH_3)_6RuCl_3$ (3.05 g) and $AlCl_3.6H_2O$ (25.9 g) were added to a large Teflon® (polytetrafluoroethylene) beaker in a dry box. $H_2O$ (25 mL) was added to the beaker and the solids were stirred until a solution was obtained. HF (30 mL) was added with stirring to the solution. The solution was then evaporated to dryness with stirring. The recovered solids were heated in argon for 3 hours at 400° C. A catalyst (9.698 g) with a nominal composition of 10% Ru/$AlF_3$ was isolated.

Example 47

$(NH_3)_6RuCl_3$ (3.05 g) and $(NH_3)_4PtCl_2.H_2O$ (0.3600 g) were added to a large Teflon® (polytetrafluoroethylene) beaker in a dry box. $H_2O$ (30 mL) was added to the beaker and the solids were stirred until a solution was obtained. Well ground alpha-$AlF_3$ (8.7000 g) was added to the beaker with stirring. The slurry was evaporated to dryness with stirring. The recovered solids were heated in argon for 3 hours at 350° C. A catalyst (9.389 g) with a nominal composition of 10% Ru/2% Pt/alpha-$AlF_3$ was isolated.

Example 48

To an alpha-$AlF_3$ (9.0 g) aqueous slurry in a Teflon® (polytetrafluoroethylene) beaker was added a solution of $Co(NO_3)_2.6H_2O$ (4.9385 g) in water. The slurry was evaporated to dryness with stirring. The dried catalyst was treated with hydrogen for 4 hours at 400° C. to obtain a catalyst with a nominal composition of 10% Co/alpha-$AlF_3$.

Example 49

$Co(NO_3)_2.6H_2O$ (9.877 g) and $AgNO_3$ (0.7874) were dissolved in a Teflon® (polytetrafluoroethylene) beaker. Well micronized alpha-$AlF_3$ (6.5000 g) was added to the beaker with stirring. The slurry was evaporated to dryness with stirring. The recovered solids were heated in hydrogen for 6 hours at 400° C. A catalyst (9.218 g) with a nominal composition of 30% Co/5% Ag/alpha-$AlF_3$(Ag) was isolated.

Example 50

The same procedure as described in Example 9 was followed using $Co(NO_3)_2.6H_2O$ (9.8765 g) and $(NH_3)_6RuCl_6$ (0.6127 g). The recovered dried solids were treated in hydrogen for 4 hours at 400° C. A catalyst (7.83 g) with a nominal composition of 20% Co/2% Ru/$AlF_3$ was isolated.

Example 51

An aqueous solution of $(NH_3)_6RuCl_6$ (3.0637 g) was slurried with a crushed commercial sample of fluorided alumina (9.0000 g) which was obtained from Engelhard (Al-4352) and which was calcined in air at 500° C. before use. The water was slowly evaporated and the residue dried at 110° C. The dried solids were treated in hydrogen for 4 hours at 400° C. A catalyst (9.887 g) with a nominal composition of 10% Ru on fluorided alumina was isolated.

TABLE 3

| Example No. | Catalyst | % Conv. | alpha | $C_5^+$ | % $C_1$ |
|---|---|---|---|---|---|
| 44 | 10% Ru/beta-$AlF_3$ | 88.8 | 0.81 | 279 | 6.2 |
| 45 | 10% Ru/theta-$AlF_3$ | 61.1 | 0.86 | 205 | 10.9 |
| 46 | 10% Ru/$AlF_3$($AlCl_3$) | 68.7 | 0.84 | 196 | 14.6 |
| 47 | 10% Ru/alpha-$AlF_3$(Pt) | 27.1 | 0.9 | 44.9 | 34.2 |
| 48 | 10% Co/alpha-$AlF_3$ | 24.6 | 0.86 | 80.7 | 20.4 |
| 49 | 30% Co/alpha-$AlF_3$(Ag) | 13.8 | 0.93 | 58.8 | 13.4 |
| 50 | 20% Co/2% Ru/$AlF_3$ | 16.5 | 0.85 | 29.8 | 27.8 |
| 51 | 10% Ru/$Al_2O_3$(F) | 64.4 | 0.89 | 241.3 | 5.7 |

While a preferred embodiment of the present invention has been shown and described, it will be understood that variations can be made to the preferred embodiment without departing from the scope of, and which are equivalent to, the present invention. For example, the structure and composition of the catalyst can be modified and the process steps can be varied.

The complete disclosures of all patents, patent documents, and publications cited herein are incorporated by reference in their entirety. U.S. patent application Ser. No. 09/314,92,/ entitled Fischer-Tropsch Processes and Catalysts Using Fluorided Supports, filed May 19, 1999 and U.S. patent application Ser. No. 09/314,811, entitled Fischer-Tropsch Processes and Catalysts With Promoters, filed May 19, 1999, are incorporated by reference in their entirety.

The foregoing detailed description and examples have been given for clarity of understanding only. No unnecessary limitations are to be understood therefrom. The invention is not limited to the exact details shown and described, for variations obvious to one skilled in the art will be included within the invention by the claims.

What is claimed is:

1. A process for producing hydrocarbons, comprising contacting a feed stream comprising hydrogen and carbon monoxide with a catalyst in a reaction zone, said catalyst comprising at least one catalytic metal for Fischer-Tropsch reactions and a support selected from the group consisting of an aluminum fluoride and fluorided aluminas.

2. The process of claim 1 wherein the catalytic metal is at least one metal selected from the group consisting of iron, cobalt, nickel, and ruthenium.

3. The process of claim 2 wherein the catalytic metal is at least one metal selected from the group consisting of cobalt, nickel, and ruthenium, and mixtures thereof, and the feed gas stream contains hydrogen and carbon monoxide in a molar ratio of about 2:1.

4. The process of claim 2 wherein the catalytic metal is iron and the feed gas stream contains hydrogen and carbon monoxide in a molar ratio of about 0.67:1.

5. The process of claim 2 wherein the support is an aluminum fluoride that is primarily alpha-$AlF_3$, beta-$AlF_3$, or a combination of alpha-$AlF_3$ and beta-$AlF_3$.

6. The process of claim 2 wherein the support is a fluorided alumina containing from 0.001% to about 10% fluorine by weight based on the weight of the support.

7. The process of claim 2 wherein the catalyst is prepared from a zero valent metal precursor.

8. The process of claim 2 wherein the catalyst is prepared from a molten metal salt.

9. The process of claim 1 wherein the support is a fluorided alumina prepared by treating an alumina with fluosilicic acid.

10. The process of claim 1 wherein the support is a fluorided alumina prepared by treating an alumina with a vaporizable fluorine-containing compound.

11. A process for producing hydrocarbons, comprising contacting a feed stream comprising hydrogen and carbon monoxide with a catalyst in a reaction zone at a temperature, pressure and space velocity effective to produce an effluent stream comprising hydrocarbons, said catalyst comprising at least one catalytic metal for Fischer-Tropsch reactions and a support selected from the group consisting of an aluminum fluoride and fluorided aluminas.

12. The process of claim 11 wherein the catalytic metal is at least one metal selected from the group consisting of iron, cobalt, nickel, and ruthenium.

13. The process of claim 12 wherein the catalytic metal is at least one metal selected from the group consisting of cobalt, nickel, and ruthenium, and mixtures thereof, and the feed gas stream contains hydrogen and carbon monoxide in a molar ratio of about 2:1.

14. The process of claim 12 wherein the catalytic metal is iron and the feed gas stream contains hydrogen and carbon monoxide in a molar ratio of about 0.67:1.

15. The process of claim 12 wherein the support is an aluminum fluoride that is primarily alpha-$AlF_3$, beta-$AlF_3$ or a combination of alpha-$AlF_3$ and beta-$AlF_3$.

16. The process of claim 12 wherein the support is a fluorided alumina containing from 0.001% to about 10% fluorine by weight based on the weight of the support.

17. The process of claim 12 wherein the catalyst is prepared from a zero valent metal precursor.

18. The process of claim 12 wherein the catalyst is prepared from a molten metal salt.

19. The process of claim 11 wherein the support is a fluorided alumina prepared by treating an alumina with fluosilicic acid.

20. The process of claim 11 wherein the support is a fluorided alumina prepared by treating an alumina with a vaporizable fluorine-containing compound.

* * * * *